United States Patent [19]
Smeekens et al.

[11] Patent Number: 6,025,542
[45] Date of Patent: *Feb. 15, 2000

[54] METHOD FOR OBTAINING TRANSGENIC PLANTS SHOWING A MODIFIED FRUCTAN PATTERN

[75] Inventors: Josephus Christianus Maria Smeekens, Driebergen; Michaël Johannes Marcus Ebskamp, De Meer; Petrus Jacobus Weisbeek, Den Dolder, all of Netherlands

[73] Assignee: Stichting Scheikundig Onderzoek in Nederland, The Hague, Netherlands

[*] Notice: This patent is subject to a terminal disclaimer.

[21] Appl. No.: 08/446,834

[22] PCT Filed: Dec. 28, 1993

[86] PCT No.: PCT/NL93/00279

§ 371 Date: Aug. 3, 1995

§ 102(e) Date: Aug. 3, 1995

[87] PCT Pub. No.: WO94/14970

PCT Pub. Date: Jul. 7, 1994

[30] Foreign Application Priority Data

Dec. 28, 1992 [EP] European Pat. Off. ............ 92204098
Apr. 15, 1993 [NL] Netherlands ......................... 9300646

[51] Int. Cl.$^7$ .............................. A01H 5/00; C12N 15/29; C12N 15/31; C12N 15/82; C12P 19/00
[52] U.S. Cl. ......................... 800/284; 800/287; 800/288; 800/289; 800/298; 435/69.7; 435/69.8; 435/101; 435/193; 435/320.1; 435/418; 435/419; 435/468; 536/23.2; 536/23.4; 536/23.6
[58] Field of Search ............................. 435/172.3, 240.4, 435/320.1, 69.7, 69.8, 419, 418, 101, 193, 468; 800/205, 250, 284, 288, 287, 289, 298; 536/23.7, 23.2, 23.4, 23.6

[56] References Cited

U.S. PATENT DOCUMENTS

| | | | |
|---|---|---|---|
| 4,801,540 | 1/1989 | Hiatt et al. | 435/172.3 |
| 4,927,811 | 5/1990 | Quarles | 514/23 |

FOREIGN PATENT DOCUMENTS

| | | |
|---|---|---|
| 9527878 | 1/1996 | Australia . |
| 2076647 | 8/1991 | Canada . |
| 2142308 | 3/1994 | Canada . |
| 2171313 | 3/1995 | Canada . |
| 0133547 | 2/1985 | European Pat. Off. . |
| 0474046 | 3/1992 | European Pat. Off. . |
| 4227061 | 2/1994 | Germany . |
| 4420223 | 5/1994 | Germany . |
| 4330960 | 3/1995 | Germany . |
| 58-201980 | 11/1983 | Japan . |
| 2072679 | 10/1981 | United Kingdom . |
| WO 89/12386 | 12/1989 | WIPO . |
| WO91/13076 | 9/1991 | WIPO . |
| WO93/07159 | 4/1993 | WIPO . |
| WO 94/04692 | 3/1994 | WIPO . |
| WO94/14970 | 7/1994 | WIPO . |
| WO94/27617 | 12/1994 | WIPO . |
| WO95/13389 | 5/1995 | WIPO . |

OTHER PUBLICATIONS

Bancal, P. et al., "Fructan chemical structure and sensitivity to an exohydrolase", *Carbohydrate Research*, 217 pp. 137–151 (1991).

Chatterton, N.J., et al. "Structure of Fructan Oligomers in Orchadgrass (*Dactylis glomerata* L.)", *J. Plant Physiology*, 142, pp. 552–545 (1993).

Nakano, Y.J. et al., "Mechanism of streptococcus Mutans Glucoysltransferases: Hybrid–Enzyme Analysis", *Journal of Bacteriology*, vol. 174, No. 17, pp. 5639–5646 (Sep. 1992).

Rastall, R.A., et al, "Synthesis of Oligosaccharides by Reversal of a Fungal B–Glucanase," *Biotechnology Letters*, vol. 14, No. 5, pp. 373–378 (May 19, 1992).

Van Der Meer, I.M., et al., "Fructan as a New Carbohydrate Sink in Transgenic Potato Plants", *The Plant Cell*, vol. 6, pp. 561–570 (Apr., 1994).

Yamamoto, S., et al. "The Mode of Synthesis of Levan by Bacillus Subtillis Levansucrase", *Agricultural and Biological Chemistry*, vol. 49, No. 2, pp. 343–349 (Feb., 1985).

Simmen, et al., "Fructan Synthesis in Excised Barley Leaves", *Plant Physiology*, vol. 101 No. 2, pp. 459–468 (1993).

Luscher, M., Purification and characterization of fructan: fructan fructosyltransferase from Jerusalem artichoke (*Helianthus tuberosus* L.), *The New Phytologist*, vol. 123, pp. 717–724 (1993).

(List continued on next page.)

*Primary Examiner*—David T. Fox
*Attorney, Agent, or Firm*—Christensen O'Connor Johnson & Kindness PLLC

[57] ABSTRACT

The present invention relates to a method for obtaining transgenic plants showing a modified fructan pattern as compared to non-transformed plants, comprising the steps of: a) preparing a DNA construct comprising one or more fructosyltransferase genes, or modified versions thereof, being operably linked to a promoter sequence active in plants and a terminator sequence active in plants; b) transforming a plant cell with the construct; and c) regenerating a transgenic plant from the transformed plant cell. Preferably, the 5' untranslated region of the fructosyltransferase gene is modified such that the expression of the fructosyltransferase is not negatively affected. The DNA construct may also comprise a targeting sequence upstream from the fructosyltransferase gene for directing the fructosyltransferase to a specific plant tissue or plant cell compartment. The fructosyltransferases produced in the transgenic plants change the fructan pattern of the plants, thus leading to different plant performance due to altered sink-source relations and yield, increased tolerance for drought, cold or other stresses, higher dry matter content, better taste and storability, and improved nutritional value. The plants are also suitable for use as raw material for fructan production.

29 Claims, 9 Drawing Sheets

OTHER PUBLICATIONS

Meiji Seika Kasha, Ltd., "Bifidus growth–stimulating substances," *Chemical Abstracts*, 100(17), p. 508, 137377f(1984).

Roberfroid, M., "Dietary fiber, inulin, and oligofructose: a review comparing their physioloical effects" *Crit. Rev. Food Sci.Nutr.* 33(2):103–148, 1993. (Medline Database Abstract).

Hirayama, M., et al., "Production and characteristics of fructo–oligosaccharaides," *Chemical Abstracts*, 120(5) : 529535, Jan.31,1994.

"Bifidus growth–stimulating substances," *Chemical Abstracts*, 100(17):137377, Apr. 23, 1994.

"Microbe belonging to Scopulariopsis generates kestose by culturing microbe in medium containing sucrose and decomposes glucose as by–product," JP–A–2163093, Jun. 22, 1990. (WPI Database Abstract).

Ebskamp, M.J.M. et al., "Accumulation of Fructose Polymers in Trangenic Tobacco", *Bio/Technology* vol. 12 (Mar. 1994), 272–275.

Cote, G.L. et al., "Purification and Properties of an Extracellular Levansucrase From *Erwinia herbicola* NRRL–1678", *Carbohydrate Research*, 190, pp. 299–307 (1989).

Geier, G. et al., "Levansucrase as a Virulence Factor in the Etiology of Fireblight", Zeller, W. (Ed.), Communications from the Federal Biological Institute of Agricultural and Forestry Berlin–Dahlem, Symposium on Fireblight, Ladenburg, Germany, Jun. 13–14, 1991, vol. 0(0), pp. 78–81 (1992). Translation provided.

John, P., "Fructan quality and fructan synthesis," *Biochemical Society Transactions*, 19(3):569–572, 1991.

Steinmetz et al 1985 Mol Gen Genet 200:220–228.

Shiroza et al 1988 J of Bacti 170(2):810–816.

Fuchs 1991 Biochem Soc. Transactions 19:555–560.

Smeekens et al 1991 Biochem Soc Transactions 19:565–569.-

METHOD FOR OBTAINING TRANSGENIC PLANTS SHOWING A MODIFIED FRUCTAN PATTERN

BACKGROUND OF THE INVENTION

The invention relates to a method for obtaining transgenic plants showing a modified fructan pattern as compared to non-transformed plants, a DNA construct for producing transgenic plants or plant tissues, the transgenic plants or plant tissues showing a modified fructan pattern as compared to non-transformed plants, the fructans isolated from the plants or tissues, the use of the transgenic plants, tissues and fructans for various applications and transgenic seed.

Plants produce many carbohydrates useful for food and non-food applications. Important examples of such carbohydrates are starch, cellulose and sucrose. These compounds are used by man either as such or in a modified form for food and industrial purposes. Crop species which produce these carbohydrates have been obtained by traditional plant breeding methods. Next to the above mentioned well known carbohydrates, many other plant carbohydrates with properties useful to man can be present in plants.

Plant carbohydrates can be divided into two groups depending on their function for the plants. The first group comprises structural carbohydrates which are usually part of the extracellular matrix. The most prominent member of this group is cellulose. The second group are the non-structural storage carbohydrate which can serve as a long term or short term (transitory) carbohydrate stores. Examples of such carbohydrates are starch, sucrose and fructans.

Fructan is a polymer consisting mostly of repeating fructose units. Fructans are mostly found in plants species which are not adapted to economic farming practices. Fructans occur in monocotyledons (esp. Poaceae, Liliaceae) and in dicotyledons (esp. Compositae) (Pollock and Cairns 1991, Ann. Rev. Plant Physiol. Plant Mol. Biol. 42, 77–101; Hendry 1987, New Phytol. 106, 201–216).

Next to its role as a plant carbohydrate reserve, other functions have been proposed for fructans. These functions include for example tolerance to dry and cold climates (cold induced desiccation) (Pontis 1989, J. Plant Physiol. 134, 148–150; Gonzales et al. 1990 New Phytol. 115, 319–323).

However, the fructans produced by plants usually have limited functionality. For these reasons fructans have as of yet not found great application in food and non-food products in spite of the recognized great commercial potential (Fuchs 1991 Biochem. Soc. Transact. 19, 555–560, A. Fuchs, ed. Inulin and Inulin-containing Crops, Elsevier, 1993) especially when compared to other carbohydrates.

One of the major problems which limit the usefulness of plant fructans is the limited range of plant species in which fructans accumulate to a substantial level. In many important current crop plants, including but not limited to sugar beet and potato, fructans are either absent or found at very low levels. Plants which do store fructans to some extent often have unfavourable agronomic properties. An example of such a plant is *Helianthus tuberosus*.

Another problem is the limited functionality of the fructans produced. The functionality is inter alia determined by the length of the fructan chains which in plants seldomly exceeds a so-called "Degree of Polymerization" (DP) of the monosaccharides of 100. Usually much smaller fructans are found and often the DP of these fructans decreases dramatically prior to harvest or following harvest and/or storage. Low DP's severely limit the usefulness of fructans in subsequent processes and can result in reduced yields.

It has now been found that it is possible to transform certain plants in order to provide for expression of fructans in suitable host plants.

SUMMARY OF THE INVENTION

The invention thus provides a method for obtaining transgenic plants showing a modified fructan pattern as compared to the non-transformed plants, comprising the steps of:

a) preparing a DNA construct comprising one or more fructosyltransferase genes, or modified versions thereof, being operably linked to a promotor sequence active in plants and a terminator sequence active in plants;

b) transforming a plant cell with the construct; and c) regenerating a transgenic plant from the transformed plant cell.

Fructosyltransferase genes are genes encoding enzymes which catalyze the production of fructose-fructose linkage. It has been proposed in the international patent application WO89/12386 to produce transgenic plants comprising a foreign gene encoding an enzyme capable of polymerizing a carbohydrate, such as for example various sucrases, in order to modify the soluble solids composition of the plant cells. WO89/12386 discloses inter alia the use of dextran sucrase. This enzyme uses sucrose as a source for the polymerization of glucose units. The present invention however relates to the polymerization of fructose units.

The present inventors found that by the presence of the 5' microbial untranslated region in the fructosyltransferase gene SacB, in which one out of frame ATG codon preceeds the initiator ATG codon, it is not possible to obtain acceptable expression levels of the said gene. It was thus found acoording to another aspect of the invention that suitable modification of the 5' untranslated region of a fructosyltransferase gene increases the expression level of the fructosyltransferase gene in the plant cell. A suitable modification comprises any modification by which the expression level of the fructosyltransferase gene is not negatively affected. In practice this means that any sequence negatively affecting the expression level is to be removed. Preferably the 5' untranslated region up to the ATG codon is entirely removed from the microbial gene.

The term "fructan pattern" refers to the distribution of the fructan in the different plant tissues and plant cell compartments such as cytosol, vacuole, apoplast etc. Some plants naturally do produce fructans whereas others do not. The fructan pattern of a plant species not producing fructans in the non-transformed plant may be changed by the introduction of a gene encoding a fructosyltransferase. The fructan distribution in a plant may also be changed by the redirection of the metabolic flow in plants or plant cells to certain plant or plant cell compartments.

Sucrose, which is the substrate for the fructosyltransferases, is a carbohydrate which is found in several different locations. It is synthesized in the cytoplasm and significant quantities can be found in cytosol, vacuole and the extracellular space (the apoplast).

Since biochemical processes in plants cells are also often limited to a single or a few cellular compartments it is desirable to promote the accumulation of the products of the newly introduced genes into a specific compartment. Therefore targeting sequences which are specific for cellular compartments must be present on the fructosyltransferases which are expressed in the transgenic plants. Specific amino acid regions for targeting to the different cellular locations have been identified and analyzed. The DNA sequences encoding these targeting regions can be coupled to the genes of interest in such a way that upon expression of the chimeric gene a protein is produced in which the targeting information is recognized and used by the cell for correct targeting to the cellular location of interest (Oakes et al. EPO 0486683, WO 91/19808, Symons et al. Bio/Technology 8, 217–221 (1990), Pen J., et al. Bio/Technology 10, 292–296 (1992)).

In a preferred embodiment of the invention the expression cassette therefore also comprises a targeting sequence for directing the fructosyltransferases to one or more specific plant or plant cell compartments. The targeting regions may be any DNA sequence having the ability of directing the fructosyltransferases to one or more of these specific plant or plant cell compartments. Examples of preferred targeting regions are the signal sequence and vacuolar targeting sequence of the carboxypeptidase Y (cpy) gene, or the signal sequence and apoplasmatic targeting sequence of the pathogenesis-related protein S gene (pr-s). By adding the targeting sequence to the DNA construct the present invention provides a method for producing transgenic plants in which the fructosyltransferase may be directed to one or more specific cell compartments thus leading to a desired fructan pattern in the plant or plant cell.

Often it is beneficial to the plant to control not only the location but also the timing of expression of the introduced genes. For example it is usually desired to limit the expression of the newly introduced enzymatic activities to specific parts of the plants, e.g. harvestable organs like tubers, fruits or seeds. Moreover it is often desired to initiate expression in these organs at a certain developmental stage. This is certainly the case when the expression of the introduced genes interferes with normal development of such organs.

The fructosyltransferases of the present invention use sucrose as a substrate to synthesize high molecular weight fructans. Many micro-organisms contain fructosyltransferases which have the ability to produce fructans (often called levans) from sucrose (A. Fuchs 1959, Thesis, University of Leiden, Han 1989 Adv. Appl. Microbiol. 35, 171–194). These enzymes can transfer fructose moieties from sucrose to a fructan acceptor molecule to produce high molecular weigth fructans. Since these fructan acceptor molecules are originally derived from sucrose they may stil contain a terminal glucose molecule. The reaction mechanism is as follows (review see Han 1989 Adv. Appl. Microbiol. 35, 171–194):

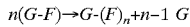

$n(G\text{-}F) \rightarrow G\text{-}(F)_n + n\text{-}1\ G$

G-F=sucrose, G=glucose, F=fructose

The glycosidic linkage which interconnects the fructose units can be a (2-1)- or a (2-6)- type depending on the particular fructosyltransferase. In micro-organisms both linkage types can be found in a single fructan molecule. Functionality of a fructan molecule depends on the type of backbone ((2-1)- or (2-6)) and the degree of branching and he degree of polymerization.

Many micro-organisms, such as bacteria, yeasts, fungi etc. contain fructosyltransferases which synthesize high DP fructans from sucrose. Usually the fructans are deposited outside the cell.

Two examples of fructosyltransferase producing bacteria are Bacillus subtilis (Steinmetz et al. 1985 Mol. Gen. Genet. 200, 220–228) and Streptococcus mutans (Shiroza, and Kuramitsu 1988 J. Bacteriol. 170, 810–816. In B. subtilis the sacB gene encodes the structural gene for levansucrase, a fructosyltransferase. This enzyme can convert sucrose into a fructose polymer with DP's which can easily exceed 10000. The linkage type found in this fructan produced by the levansucrase is mainly of the (2-6)-type with extensive (2-1)-branching.

In another micro-organism S. mutans the ftf gene encodes a fructosyltransferase which can also produce fructans of very high DP. The fructose units in this fructan are mainly (2-1)-linked type with (2-6)-branching (Rosell and Birkhed 1974 Acta Chem. Scand. B28, 589).

Bacterial fructosyltransferases have a relatively low Km for sucrose, approx. 20 mM. Sucrose concentrations in most plants is considerably higher and therefore these enzymes should be active in plants. Another important property of bacterial fructosyltransferases is their ability to synthesize levans at low temperatures up to 0° C. (Tanaka et al. 1978 Agric. Biol. Chem. 42, 323–326). Plants often encounter such temperatures but in such conditions these enzymes could still be active.

The preferred structural fructosyltransferase gene(s) largely depend on the requirements for degree of polymerisation of the polymer and its degree of branching of the fructans for the various uses.

The present invention is not limited to microbial fructosyltransferases but it is also possible to use fructosyltransferases originating from plants or any other prokaryotic or eukaryotic source.

In plants fructan biosynthesis and degradation has been investigated especially in Helianthus tuberosus and in several grasses (Pollock and Cairns 1991, Ann. Rev. Plant Physiol. Plant Mol. Biol. 42, 77–101; Pollock 1986, New Phytol. 104, 1–24). In different plant families different fructans types are synthesized, linear or branched, with 2-1 and 2-6 glycodsidic linkages between the fructose molecules. In plants fructans are stored in the vacuoles. The substrate for fructan biosynthesis is sucrose, however the affinity of plant enzymes for sucrose is lower (approx. Km 100) than is the case with the bacterial enzymes. The plant enzymes involved in fructan metabolism are very cold tolerant (Pontis 1989, J. Plant Physiol. 134, 148–150; Gonzales et al. 1990 New Phytol. 115, 319–323) and may therefore be very useful in certain applications.

Nearly all plants are capable of sucrose synthesis which takes place in the cytosol. Sucrose is the major carbohydrate translocation sugar and it is transported from source (net carbohydrate exporting tissue) to sink (net carbohydrate importing tissue) via the vascular system. This transport often includes transfer of sucrose through the extracellular space, the apoplast. Moreover sucrose can also be used by plants for carbohydrate storage. In the latter case it usually accumulates in the vacuoles of the plant cells, e.g. in the roots of sugar beet plants. In conclusion, there are two important cellular locations where sucrose is found in plant cells: the cytosol and the vacuole. In addition, substantial amounts of sucrose is present in the extracellular space (the apoplast) of many plants.

The preferred targeting region should target the fructosyltransferase to compartments where substrate is available such as vacuoles, cytosol and the apoplast, respectively. For high fructan accumulation for instance the vacuole is the preferred compartment. For other purposes (e.g. drought and cold resistance) fructan accumulation in the cytosol or apoplast may be preferable.

Especially the accumulation of sucrose in the vacuoles of many plants makes this cellular location ideally suited for the induction of fructan biosynthesis by microbial or plant enzymes.

A preferred embodiment of the invention therefore provides a method for the vacuolar expression of microbial, plant or other fructosyltransferases in transgenic plants. This method involves the fusion of DNA sequences which encode plant specific expression signals, a vacuolar localization signal and microbial, plant or other fructosyltransferases.

Two other compartments in which sucrose is available, the cytosol and the apoplast, can also be important sites for fructan accumulation. This can be achieved by the direction of microbial, plant or other fructosyltransferases to the cytosol or apoplast. For cytosolic expression no cellular routing information is required; expression of the mature enzymes is sufficient. For apoplastic expression of fructosyltransferases a targeting region must be added to the enzyme which targets the enzyme to the apoplast.

For expression in plants of the modified fructosyltransferase gene promoter signals must be added to the DNA construct. Such expression promoters can be specific for a certain cell type or can be active in a wide array of cell types. In addition, the timing of expression can be determined by the use of for example developmental-specific promoters. One commonly used promoter for gene expression in plants is the 35S Cauliflower Mosaic Virus promoter which is active in many cell types in the plant independent of the developmental state of the plant. Another promoter for gene expression which may be used when practicing the present invention is the granule-bound starch synthase promoter of the potato.

The preferred promoter may be a tissue-specific or constitutive promoter, strong or weak, depending on target plant and objective. For fructan production in storage organs the preferred promoter would be a sink-specific, strong promoter.

To further improve transcription levels the promoter is often modified to contain an enhancer duplication.

The translation of the mRNA's may be improved by adding a translational enhancer such as the Alfalfa Mosaic virus RNA4 translational enhancer signal which must be present in the transcribed 5' untranslated region.

For proper termination of transcription a plant specific terminator sequence must be added to the constructs. An example of such a sequence is the nopaline synthase gene termination sequence.

The present invention is not limited to naturally occuring fructosyltransferases but may equally well be performed by using modified versions thereof. Modifications may influence the activity of the fructosyltransferases in such a way that e.g. the degree of polymerization or the structure of the fructan produced is altered.

The induced accumulation of fructans in transgenic plants using the principle described above will allow for the extraction of fructans from these plants for the purpose of fructan production. Fructans can be accumulated in these plants e.g. in harvestable organs such as roots, beets, leaves, stems, tubers, fruits and seeds.

Genetically modified crop plants which incorporate the fructosyltransferase-encoding constructs mentioned above will allow for the efficient production of a high quality carbohydrate polymer useful to man.

The invention provides a method which provides plants with new biosynthetic capacities which enable them to produce and accumulate fructan. Such plants have improved performance due to altered sink-source relations and yield, or improved performance under abiotic and biotic stresses. Such stresses include but are not limited to drought, light, temperatures, diseases and pests. Improved performance under normal or stress conditions include, but are not limited to, higher dry matter content, better taste or storability, improved nutritional value, etc. Such plants can be suitably used as raw material for fructan production.

According to the present invention a single fructosyltransferase gene or a combination of fructosyltransferase genes of either prokaryotic or eukaryotic origin may be used. These genes can encode enzymes for the biosynthesis of a wide range of fructans.

The present invention further relates to seeds, cuttings, tubers, bulbs, or other parts of the transgenic plants which are useful for the continuous production of further generations of said plants.

The fructans produced using transgenic plants of the present invention may be used in various food and non-food applications. Examples include but are not limited to human and animal food products, in the production of fructose syrups, in the production of chemicals and plastics either as such or in a modified form.

DETAILED DESCRIPTION OF THE INVENTION

Figure 1:
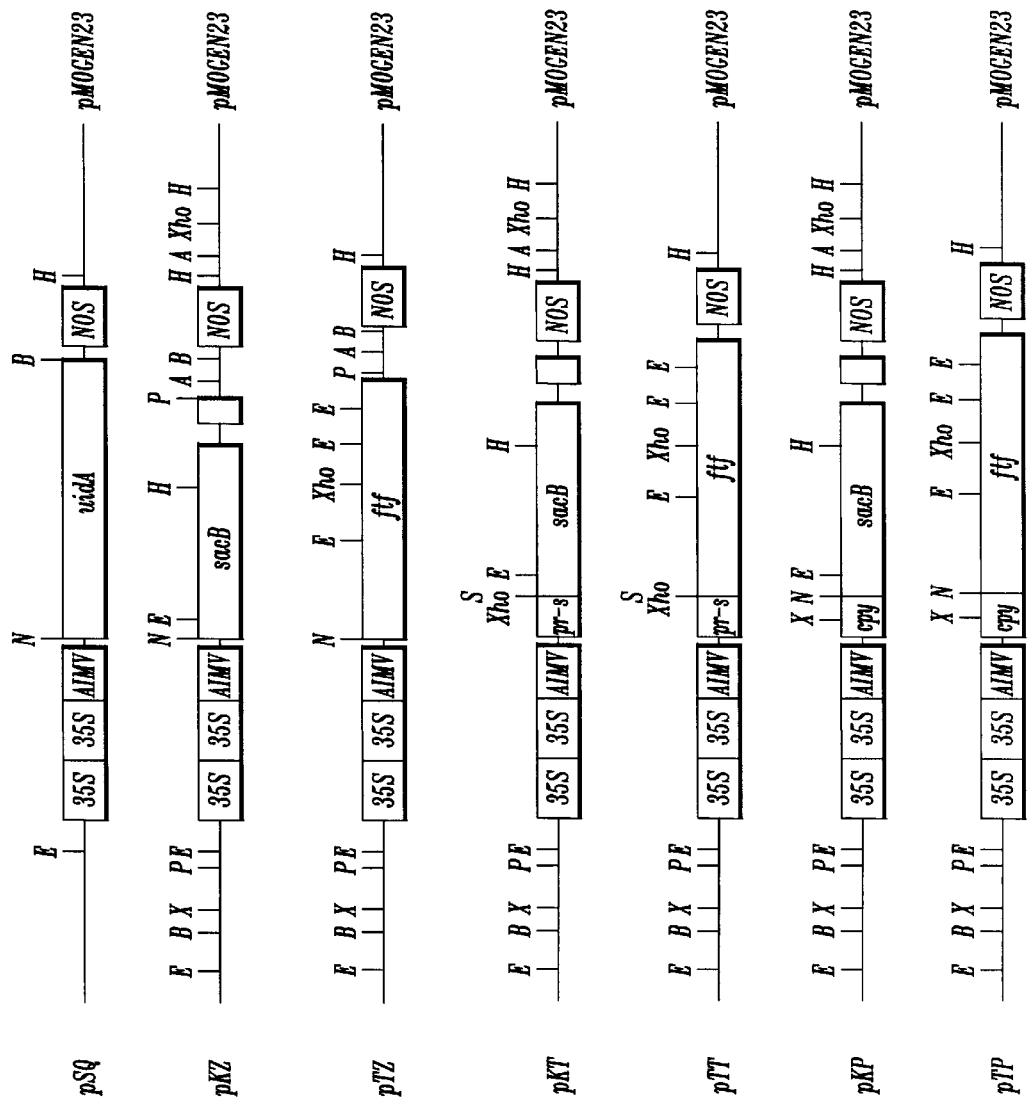
FIG. 1 is a summary of the constructs.
Figure 2:
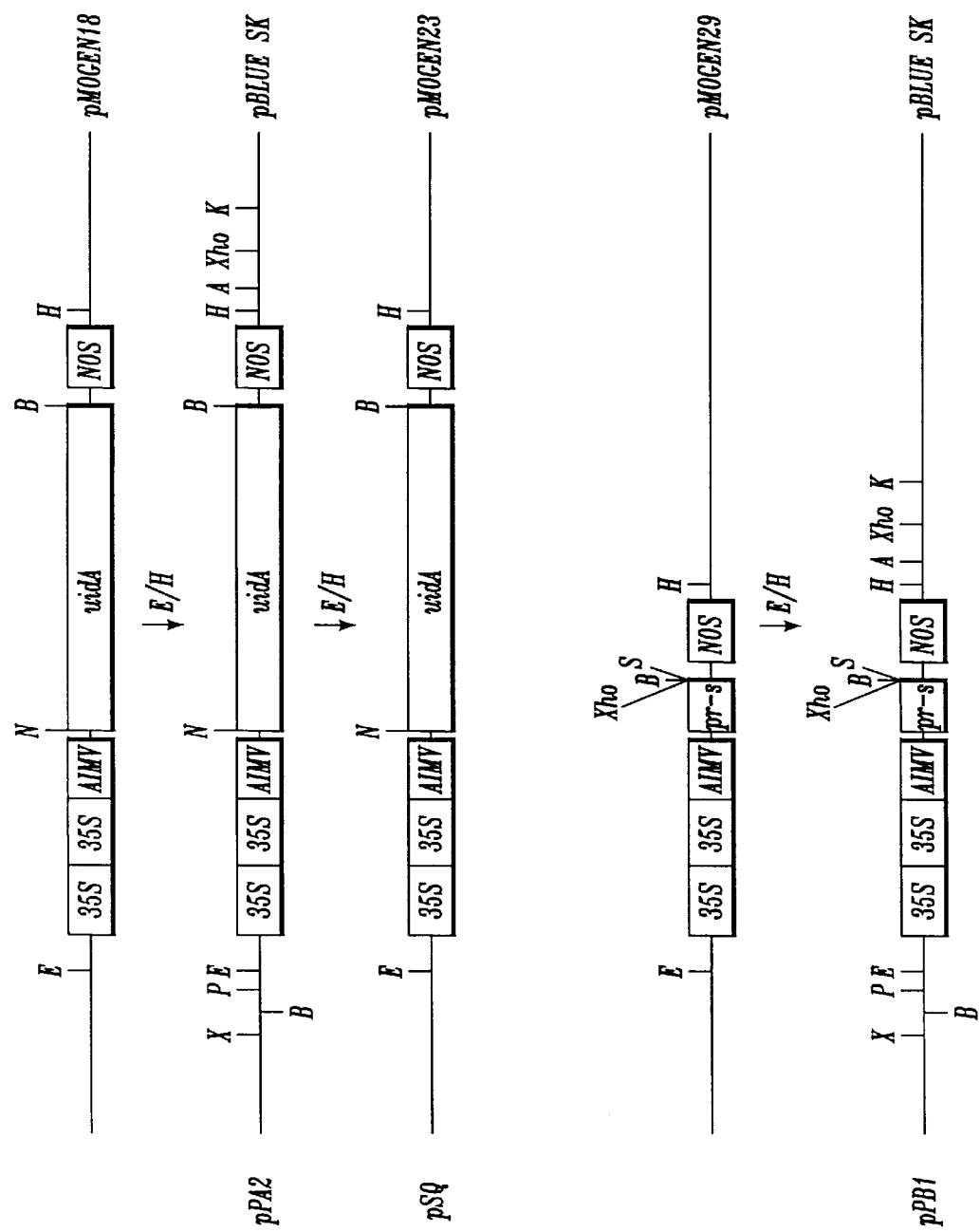
FIG. 2 shows the construction of plasmids pPA2 and pPB1.
Figure 3:
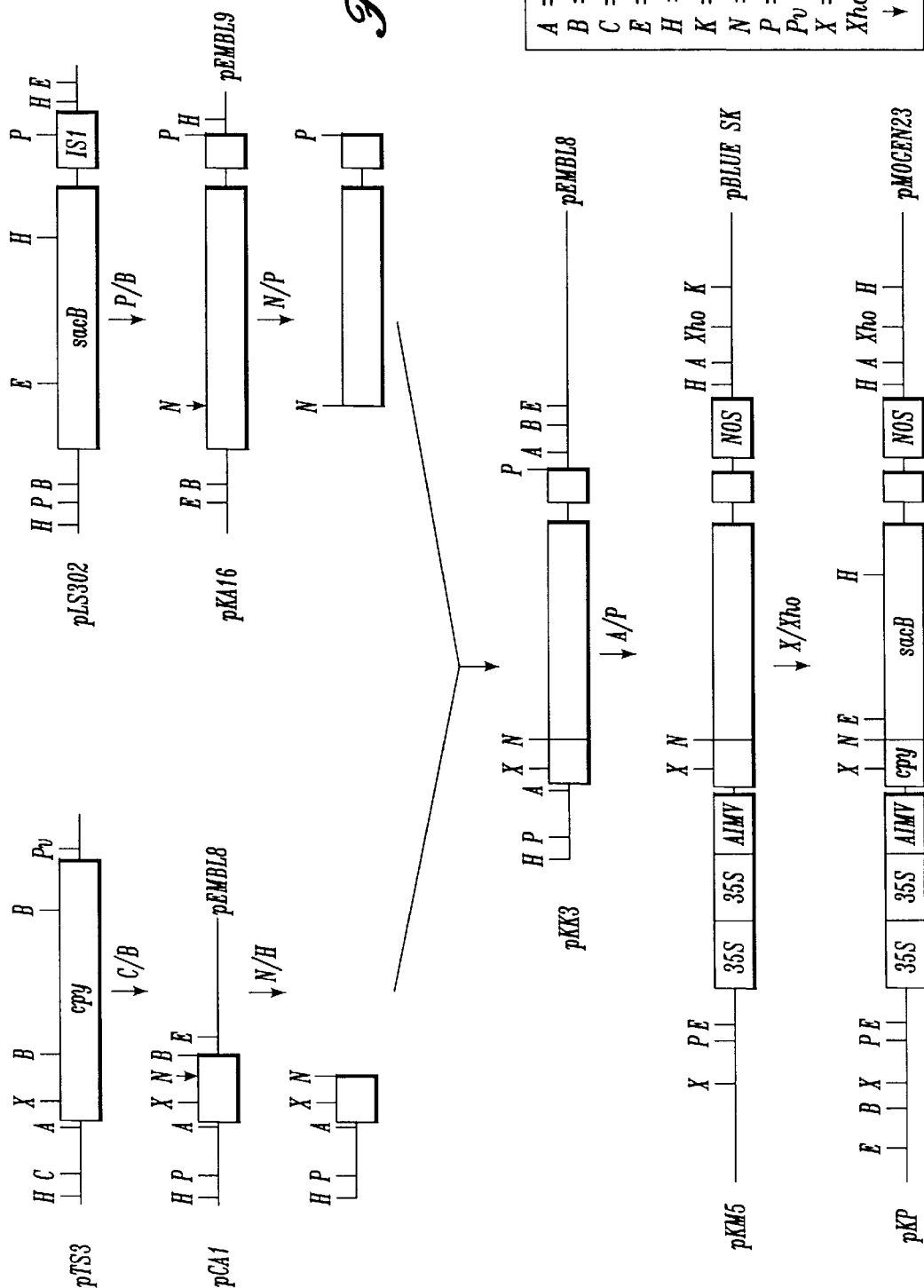
FIG. 3 shows the construction of 35S-cpy-sacB-NOS in binary vector (pKP)
Figure 4:
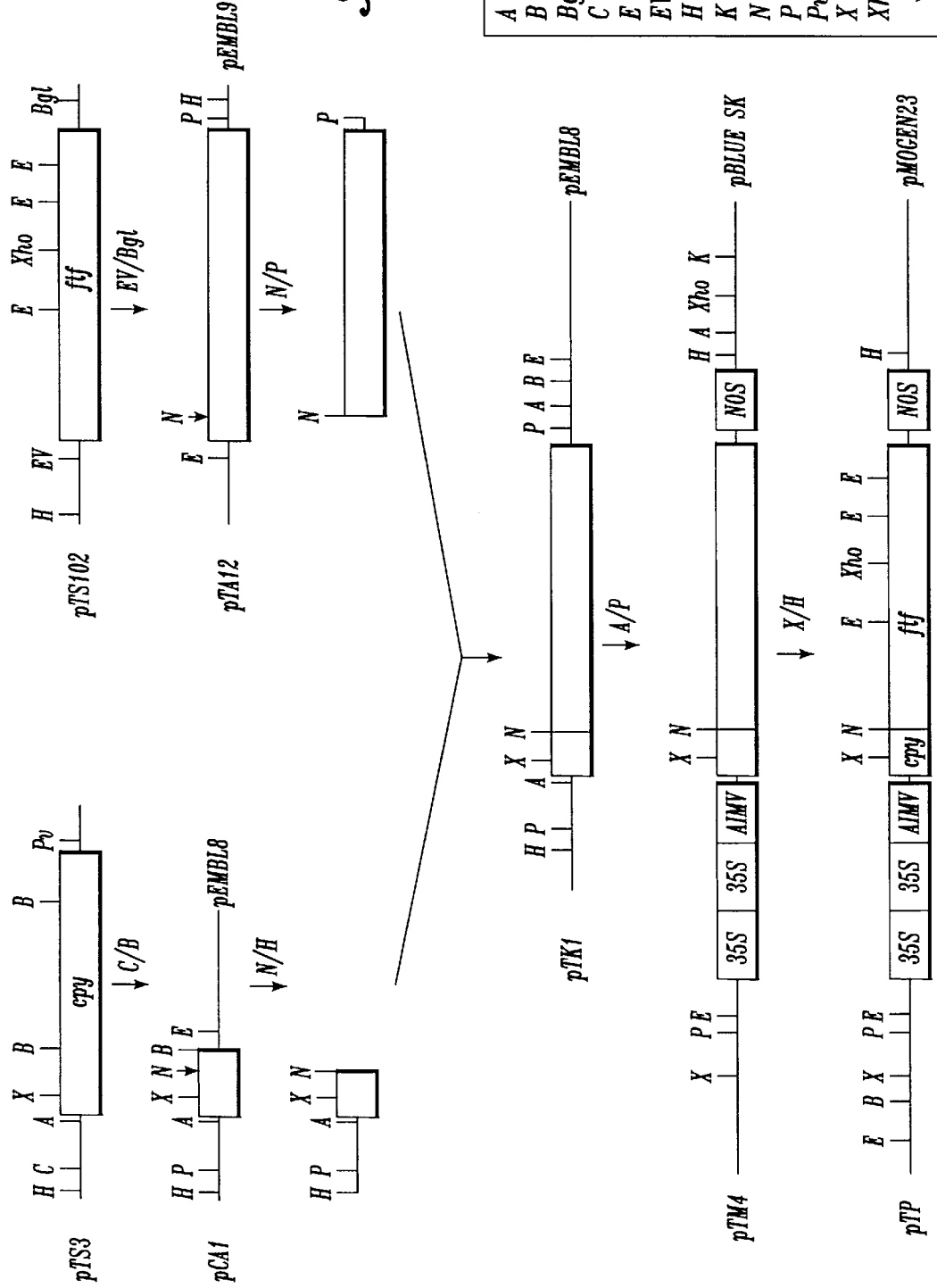
FIG. 4 shows the construction of 35S-cpy-ftf-NOS in binary vector (pTP)
Figure 5:
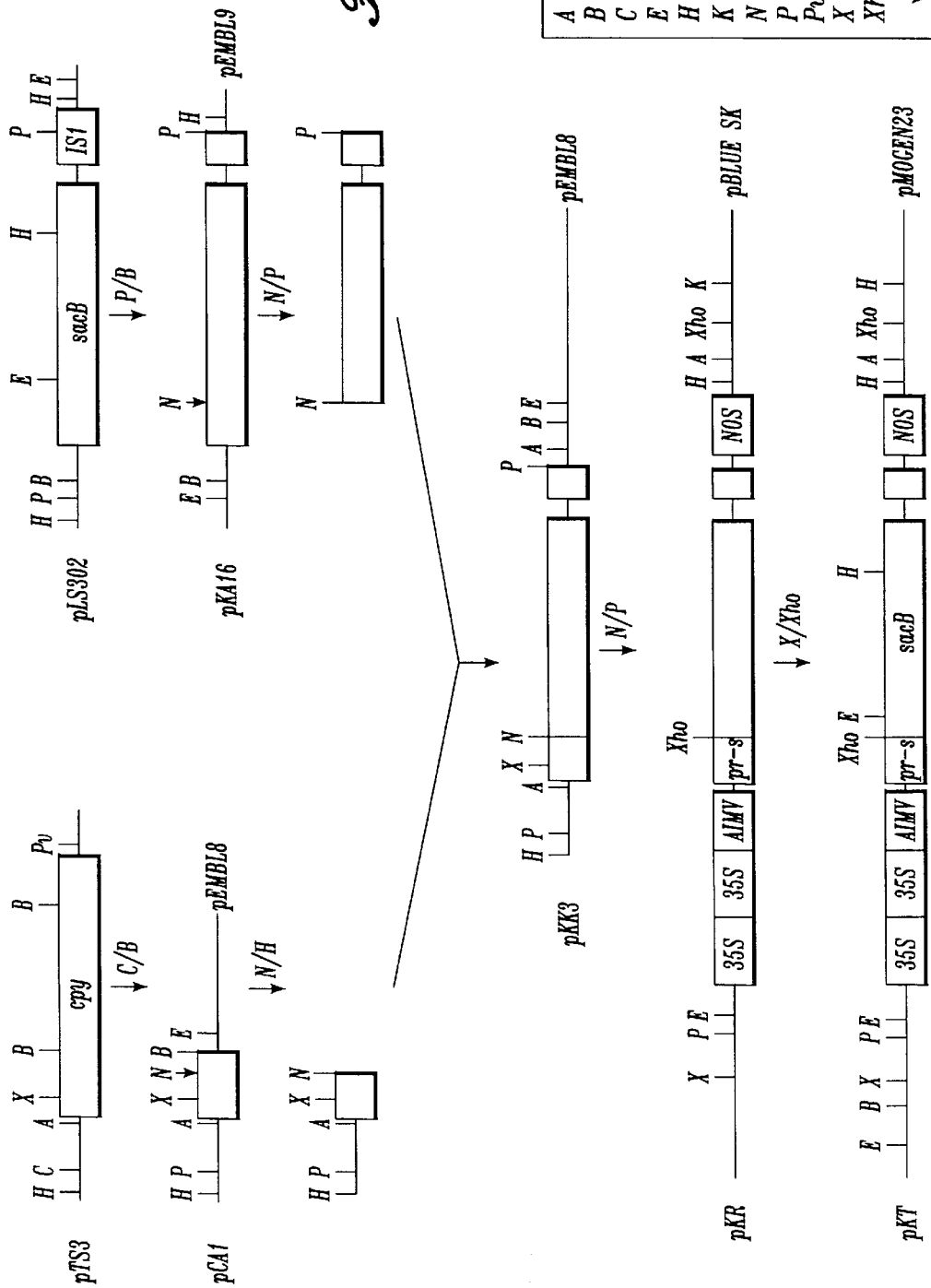
FIG. 5 shows the construction of 35S-pr-s-sacB-NOS in binary vector (pKT)
Figure 6:
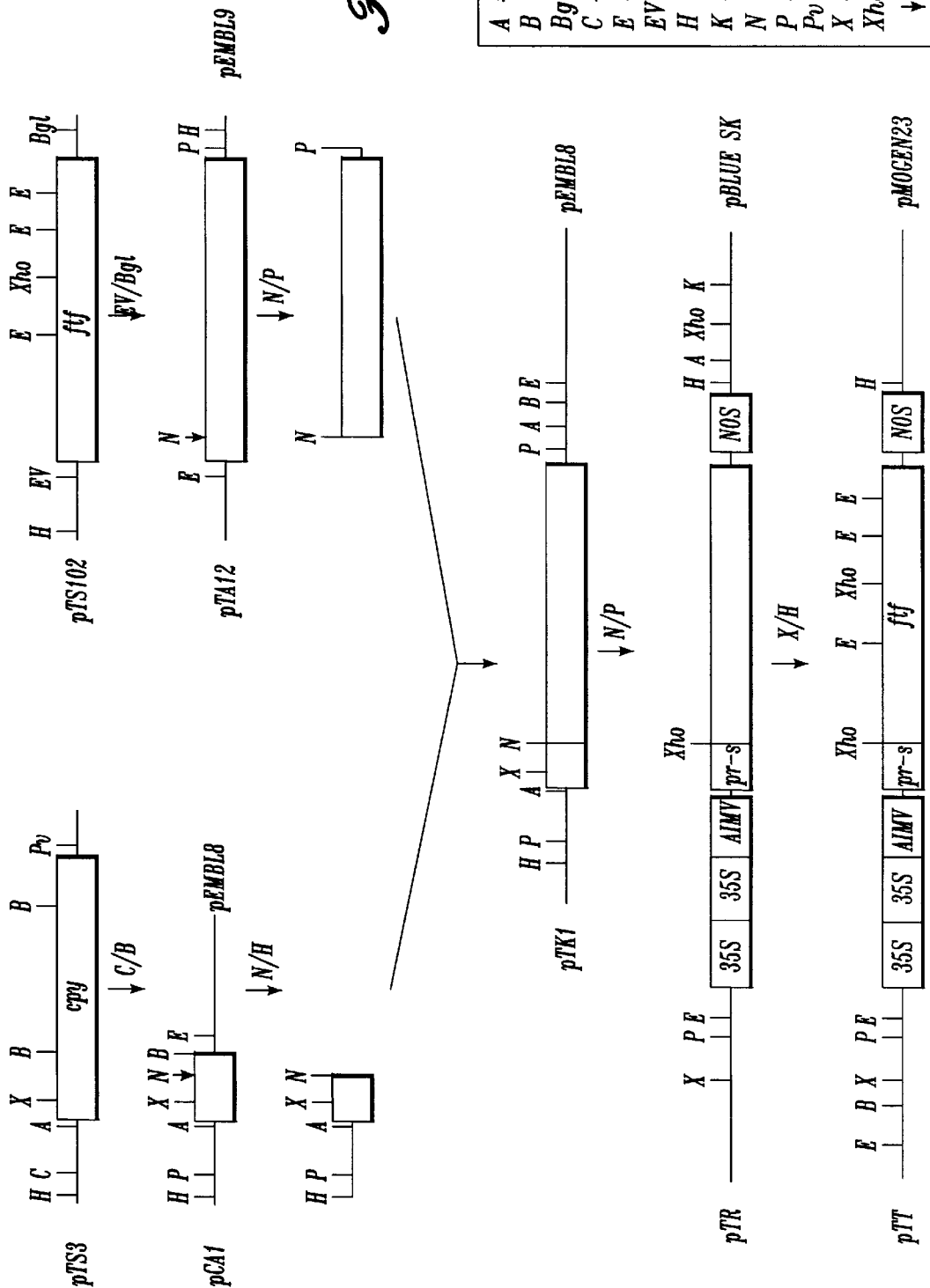
FIG. 6 shows the construction of 35S-pr-s-ftf-NOS in binary vector (pTT)
Figure 7:
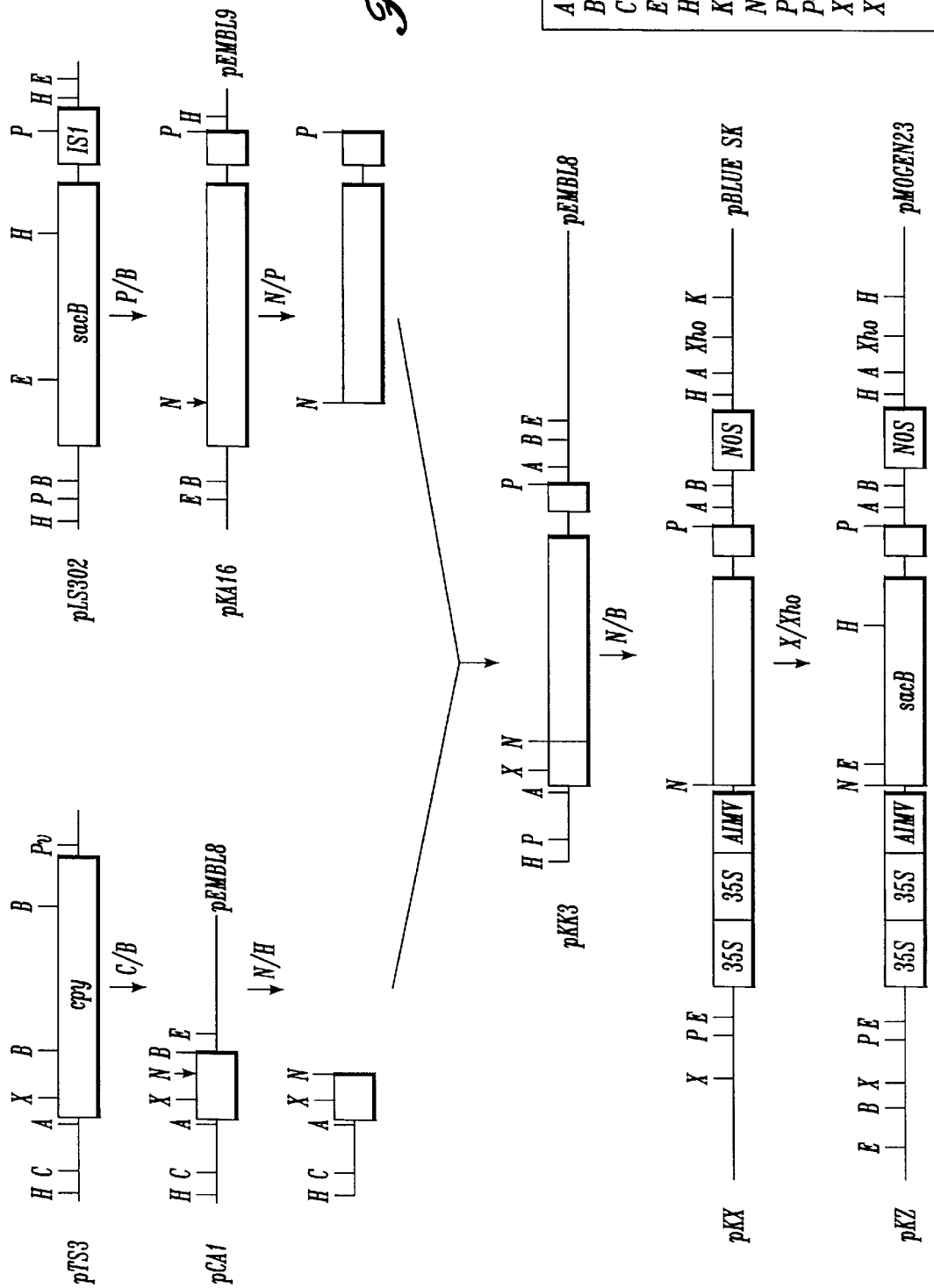
FIG. 7 shows the construction of 35S-sacB-NOS in binary vector (pKZ)
Figure 8:
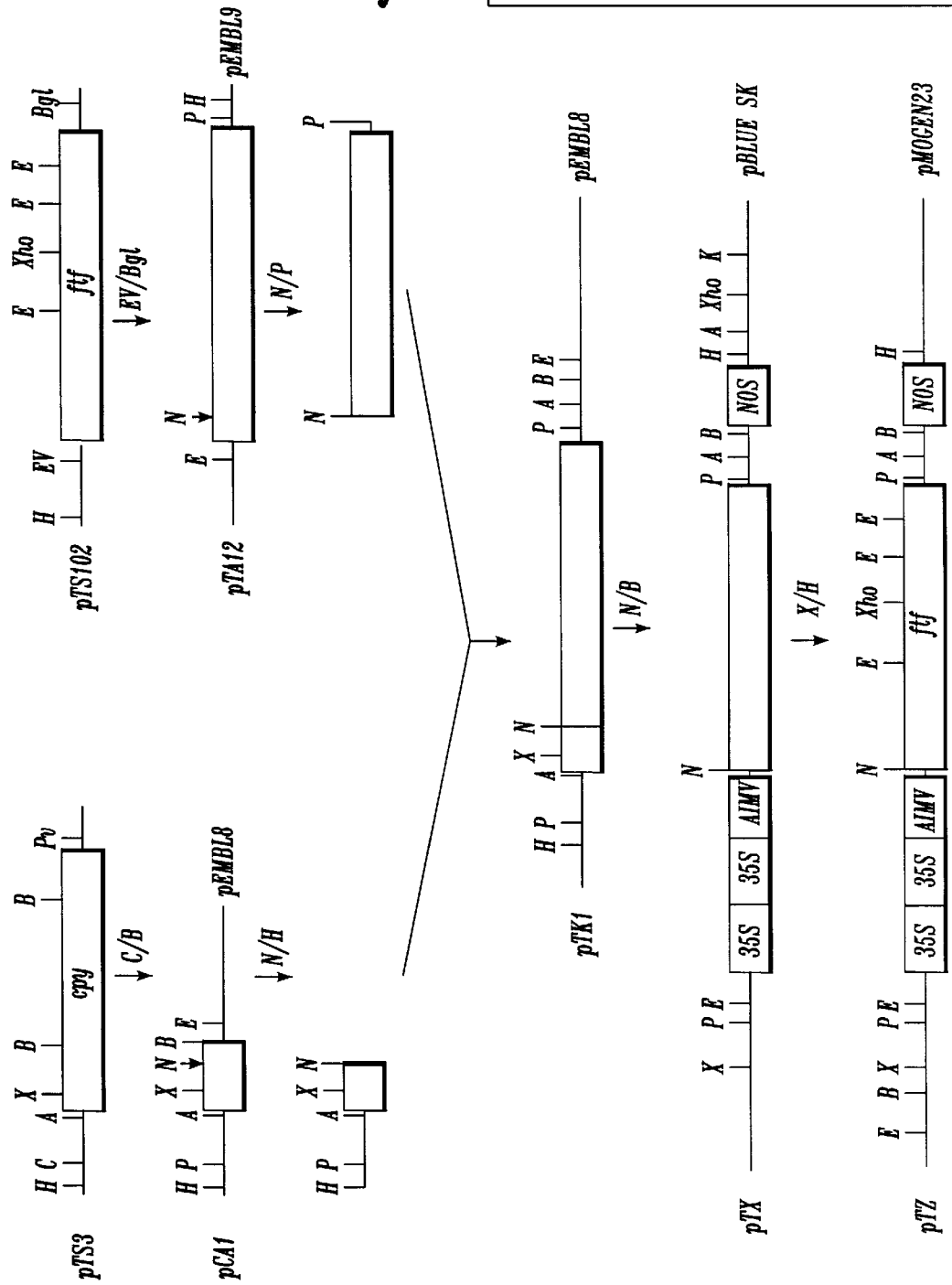
FIG. 8 shows the construction of 35S-ftf-NOS in binary vector (pTZ)

The present invention will be illustrated in the following examples which are in no way intended to limit the scope of the present invention.

EXAMPLE 1

Expression of sacB Gene in the Vacuole

1. Selection of genes to be used.

To create fructan-producing transgenic plants, genes encoding proteins capable of producing fructans were selected. One of these genes, levansucrase, encoded by the sacB gene of *Bacillus subtilis* (Steinmetz M. et al. Mol. Gen. Genet. 200:220–228(1985)), was used. This enzyme produces mainly branched fructans of the (2-6)-linkage type in the presence of sucrose.

Since sucrose in plant cells can accumulate in vacuoles, this is a preferred site for fructan production. To direct the levansucrase to the vacuole the targeting region of carboxypeptidase Y (Valls L. A. et al. Cell 48, 887–897 (1987)) was selected.

2. Construction of 35S-cpy-sacB-NOS in binary vector (pKP).

Plasmid pLS302 has been described by Steinmetz M. et al., supra. The levansucrase (sacB) gene was cloned from this plasmid as a BamHI and PstI fragment into the multiple cloning site of pEMBL9 (Dente L. et al. Nucleic Acids Res. 11, 1645–1655 (1983)) in the corresponding BamHI and PstI sites resulting in plasmid pKA16. General DNA cloning methodology has been described (Sambrook J. et al. Cold Spring Harbour, N.Y. Cold Spring Harbour Laboratory (1989)).

To create a NcoI site near the mature processing site of the levansucrase gene at nucleotide position 550 (Steinmetz M. et al. supra) site directed mutagenesis as described by Kramer W. et al. (Nucleic Acids Res. 12, 9441–9456 (1984)) was performed with the following oligonucleotide 5'-GCAACTCAAGCCATGGCGAAAGAAACG3-' resulting in plasmid pKD22.

At the amino acid position −2 relative to the mature processing site (nucleotide position 544) a phenylalanine was hereby changed to a methionine. The NcoI-PstI fragment, in which the sequence encoding the mature levansucrase protein is present, was used for further cloning.

Plasmid pTS3 containing the carboxypeptidase Y (cpy) gene has been described by Valls L. A. et al., supra.

The first part of the cpy gene was cloned from this plasmid as a ClaI (−695) and BamHI (462) fragment into the multiple cloning site of pEMBL8 (Dente L. et al., supra), in the corresponding AccI and BamHI site resulting in plasmid pCA1.

To create a NcoI site near the mature processing site downstream of the vacuolar targeting sequences of the cpy gene at nucleotide position 330 (Valls, L. A. et al. supra), site directed mutagenesis as described by Kramer W. et al. (supra) was performed with the following oligonucleotide: 5'-CGTGTCAACAAGACCATGGACCCTAA-3'. The resulting plasmid pCB50 contains the first part of the cpy gene with a NcoI site at the mature processing site. At the amino acid position +2 relative to the mature processing site at nucleotide position 334 a isoleucine was replaced by a threonine. At amino acid position +3 relative to the mature processing site at nucleotide position 337 a lysine was replaced by a methionine. The HindIII-NcoI fragment in which the sequence encoding the vacuolar targeting part of carboxypeptidase Y protein is present, was used for further cloning.

The vacuolar targeting sequence of the cpy gene was fused to the mature sequence of the levansucrase gene using a threepoint ligation (Sambrook J. et al. supra).

The following fragments were used in equimolar concentrations:
the HindIII-NcoI fragment of the cpy gene (encoding the vacuolar targeting sequence), the NcoI-PstI fragment of the sacB gene, and the fragment containing the vector of pEMBL8 which was digested with HindIII and PstI. The resulting plasmid pKK3 encodes the in frame construct of the carboxypeptidase Y-levansucrase fusion. The correct reading frame of the fusion gene was confirmed by sequence analysis.

The plasmid pMOG18 which contains a plant-specific 35S promoter with enhancer duplication and sequences which enhance translation of the mRNA has been described by Symons et al., Bio/Technology 8, 217–221 (1990). It contains the 35S-promotor/uidA-gene/NOS-terminator construct. A pBluescript II SK (Stratagene, San Diege Calif.) from which the internal BamHI site had been removed, by cutting with BamHI and filling in of the sticky ends with Klenow and religation, was used for further cloning. The 35S-uidA-NOS fragment was obtained by digestion with EcoRI and HindIII of pMOG18 and was cloned in this pamHI-pBluescript into the corresponding EcoRI and HindIII site resulting in plasmid pPA2. This plasmid was digested with NcoI and BamHI to remove the uidA gene. The resulting vector was treated with S1-nuclease to remove overhanging ends and then dephosphorylated. From plasmid pKK3 the fragment containing the cpy-sacB fusion was isolated by digestion with AccI and PstI. These sites were blunted with Klenow. These two fragments were ligated resulting in plasmid pKM5. pKM5 contains the 35S-promotor/ cpy-sacB-gene-fusion/NOS-terminator construct.

This plasmid, pKM5, was digested first with XhoI and then partially digested with XbaI. The fragment containing the complete construct (35S-cpy-sacB-NOS) was cloned into the XbaI and XhoI site of pMOG23 (Symons et al. supra), a binary plant vector pBIN19 derivative (Bevan M., Nucl. Acids Res. 12: 8711–8721) resulting in plasmid pKP.

3. Transformation of pKP to tobacco plants.

The pKP plasmid was conjungated into *Agrobacterium tumefaciens* LB4404 (Hoekema A. et al., Nature 303, 179–180 (1983)) in a triparental mating event using the helper plasmid pRK2013 (Lam S. T. et al., Plasmid 13, 200–204 (1985)). The construct was introduced into *Nicotiana tabacum* var. Petit Havanna (SR1) using the leaf disc transformation method (Horsch R. B. et al., Science 227, 1229–1232 (1985). Regenerated plants, named KP plants, were selected for kanamycin resistance and grown on MS medium (Murashige and Skoog Physiol. Plant. 15, 473–497 (1962)) containing glucose instead of sucrose. Thereafter plants were grown on soil in the greenhouse and analysed.

4. Analysis of KP plants.

Plants were grown in the greenhouse and leaf material was cut off and ground in an eppendorf tube. Following centrifugation (2' 16000 rpm) 1 µl of supernatant was spotted on TLC (Cairns A. J. and Pollock C. J. New Phytol. 109, 399–405 (1988)). The TLC was developed three times in 85:15 acetone:water and then treated with urea-spray as described (Wise C. S. et al. Analytical Chemistry 27, 33–36 (1955)). This method preferentially stains fructose and fructose-containing polymers.

Fructose polymers were never detected in non-transformed plants nor in plants transformed with unrelated constructs. Screening of the transformants, using this method, showed extensive accumulation of fructans in these plants. Fructan expression levels varied between individual plants transformed with the same construct as is normally found in plant transformation experiments. This variation of expression levels depends mainly on the genomic integration site (position effect).

The fructans accumulating in these plants were further studied by isolation of larger quantities (Livingstone III D. A., Plant Physiol. 92, 767–769 (1990)). This fructan was analysed by sizing on a FPLC Superose 6HR 10/30 column (Pharmacia) and fructans were detected in the void volume indicating a degree of polymerisation of >25.000 fructose units. Fructan produced by *Bacillus subtilis* levansucrase similarly elutes in the void volume of the Superose column.

Figure 9:
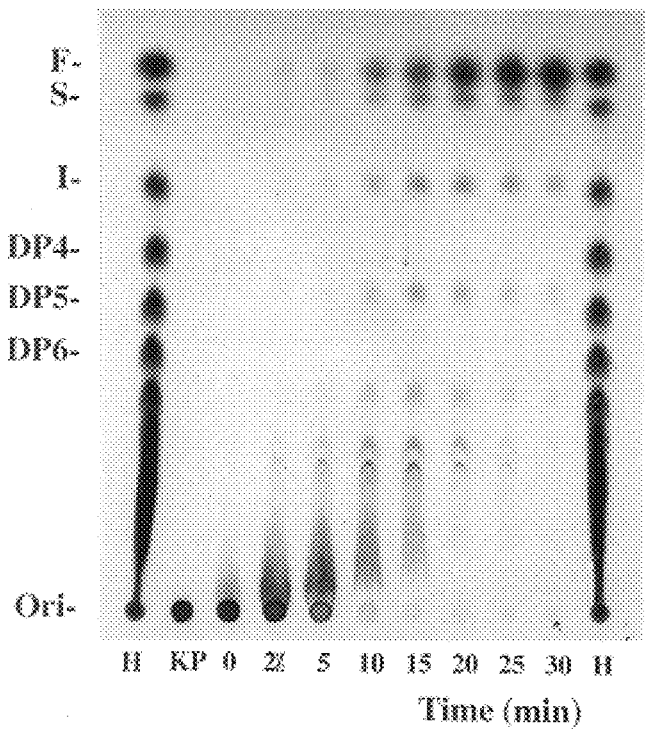
FIG. 9 is an example of a partial acid hydrolysis of fructan isolated from a transgenic KP tobacco plant. This partial hydrolysis pattern is identical to that of fructans produced by *Bacillus subtilis*. F=fructose, S=sucrose (disaccharide), I=1-kestose (trisaccharide) DP4, 5 and 6=tetrapenta and hexasaccharides, respectively, H=*Helianthus tuberosus* tuber extract used as standard.

Partial fructan degradation by acid degradation (See FIG. 9) shows a characteristic pattern of hydrolysis products. The purified plant and bacterial fructans show identical degradation patterns on TLC. Full acid hydrolysis followed by HPLC analysis on an Aminex HPX87C column (Biorad) at 85° C. using water as eluent shows this fructan to be composed of fructose.

The purified fructans were also analysed by proton-NMR. Fructan isolated from transgenic plants showed no differences in peak pattern when compared with fructan synthesised by levansucrase from *Bacillus subtilis*.

We have not found any fructan hydrolysing activity in several plant species (tobacco, sugar beet, tomato, potato). When plant protein extracts are incubated with fructan for prolonged periods of time in phosphate-citrate buffer at pH 5.0 no fructose is released.

Upon senescence plant fructans remain present in the transgenic plants, confirming the stability seen with protein extracts. Fructans accumulate throughout the plant which is in accordance with the unspecific 35S promoter activity in transgenic plants.

Transgenic plants set seed normally. Seed germination is identical to untransformed plants and the construct is stably inherited by the following generation which similarly produce fructans.

EXAMPLE 2

Expression of ftf Gene in the Vacuole

1. Selection of the genes.

To create fructan-producing plants, genes encoding proteins capable of producing fructans were selected. Another gene, fructosyltransferase encoded by the ftf gene of *Streptococcus mutans* (Shiroza T. and Kuramitsu H. K., J. Bacteriol. 170, 810–816 (1988)), was used. This enzyme produces mainly branched fructans of the (2-1)-linkage type in the presence of sucrose. Since sucrose in plant cells can accumulate in vacuoles, this is a preferred site for fructan accumulation. A gene encoding a protein capable of targeting itself to the vacuole was selected: carboxypeptidase Y (Valls L. A. et al., supra). From this gene the signal sequence and vacuolar targeting sequence were used as described in Example 1.

2. Construction of 35S-cpy-ftf-NOS in binary vector (pTP)

Plasmid pTS102 has been described by Shiroza T. and Kuramitsu H. K. (supra). The fructosyltransferase (ftf) gene was cloned from this plasmid as an EcoRV and BqlII fragment into the multiple cloning site of pEMBL9 (Dente L. et al., supra) in the compatible SmaI and BamHI sites resulting in plasmid pTA12.

To create a NcoI site near the mature processing site of the ftf gene (nucleotide position 783 (Shiroza T. and Kuramitsu H. K. (supra)) site directed mutagenesis as described by Kramer W. et al. (supra) was performed with the following oligonucleotide:
5'-GGCTCTCTTCTGTTCCATGGCAGATGAAGC-3'
resulting in plasmid pTD2.

At amino acid position +1 (nucleotide position 783) relative to the mature processing site a glutamine was hereby changed to a methionine. The NcoI-PstI fragment, in which the sequence encoding the mature fructosyltransferase protein is present, was used for further cloning.

From plasmid pCB50 (as described in Example 1) the HindIII-NcoI fragment in which the sequence encoding the vacuolar targeting part of carboxypeptidase Y protein is present, was used for further cloning.

The vacuolar targeting sequence of the cpy gene was fused to the mature sequence of the fructosyltransferase gene using a threepoint ligation (Sambrook J. et al., supra). The following fragments were used in equimolar concentrations:
the HindIII-NcoI fragment of the cpy gene (encoding the vacuolar targeting sequence), the NcoI-PstI fragment of the ftf gene, and the fragment containing the vector of pEMBL8 which was digested with HindIII and PstI. The resulting plasmid pTK1 encodes the in frame construct of the carboxypeptidase Y fructosyltransferase fusion. The fusion is in the correct reading frame which was confirmed by sequence analyses.

Plasmid pPA2 described in Example 1 was digested with NcoI and BamHI to remove the uidA gene. The resulting vector was treated with S1-nuclease to remove overhanging ends and then dephosphorylated. From plasmid pTK1 the fragment containing the cpy-ftf fusion was isolated by digestion with AccI and PstI. These sites were blunted with Klenow. These two fragments were ligated resulting in plasmid pTM4. pTM4 contains the 35S-promotor/cpy-ftf-gene-fusion/NOS-terminator construct.

This pTM4 was digested with XhoI and then partially digested with XbaI. The fragment containing the complete construct (35S-cpy-ftf-NOS) was cloned into the XbaI and HindIII site of pMOG23 (Symons et al. supra), a binary plant vector pBIN19 derivative (Bevan M., supra) resulting in plasmid pTP.

Transgenic plants, named TP plants, which contain the construct described were generated as described in Example 1.

3. Analysis of TP plants.

Screening of the transformants, using the TLC method as in Example 1, showed accumulation of fructan with the normal variation due to position effect. The fructans accumulating in these plants were further studied by isolation of larger quantities (Livingstone III D. A., supra). This fructan was analysed by sizing on a FPLC Superose 6HR 10/30 column (Pharmacia) and fructans were detected in the void volume indicating a degree of polymerisation of >25.000 fructose units. Fructan produced by *Streptococcus mutans* fructosyltransferase similarly elutes in the void volume of the Superose column. Similarly partial fructan degradation by acid degradation shows a characteristic pattern of hydrolysis products. The purified plant and bacterial fructans show identical degradation patterns on TLC. Full acid hydrolysis followed by HPLC analysis on an Aminex HPX87C column at 85° C. using water as eluent shows this fructan to be composed of fructose.

As in Example 1, senescing plants still contain fructans. Similarly seeds are fertile and the fructan producing property is inherited by the following generation.

EXAMPLE 3

Expression of sacB in the Apoplast

1. Selection of the genes.

To create plants which produce fructans, genes encoding proteins capable of producing fructans were selected. One of these genes, levansucrase encoded by the sacB gene (Steinmetz M. et al., supra) and described in Example 1, was used.

Since sucrose in tobacco plants is transported through the apoplast to the phloem, the intercellular space (apoplast) is a preferred site for fructan accumulation. A gene encoding a protein capable of targeting itself to the apoplast was selected: the pathogenesis-related protein S, encoded by the pr-s gene (Cornelissen B. J. C. et al. Nature 321, 531–532 (1986)). From this gene the export signal sequence was used.

2. Construction of 35S/pr-s-sacB/NOS in binary vector (pKT).

Plasmid pMOG29 has been described by Pen J., et al. (Bio/Technology 10, 292–296 (1992)). The pathogenesis-related protein S (pr-s) gene (Cornelissen B. J. C. et al., sunra; Van Kan J. A. L. et al. Plant Mol. Biol. 12, 153–155 (1989)) has a signal sequence which can target proteins to the intercellular space, the apoplast (Pen J., et al., supra). The plasmid pMOG29 contains the 35S-promotor/pr-s-sequence/NOS-terminator construct. A pBluescript II SK (Stratagene) from which the internal BamHI site had been removed, by cutting with BamHI and filling in of the sticky ends with Klenow and religation, was used for further cloning. The 35S-promotor/pr-s-sequence/NOS-terminator construct was obtained by digestion with EcoRI and HindIII of pMOG29 and was cloned in this pBluescript into the corresponding EcoRI and HindIII site resulting in plasmid pPB1. Plasmid pPB1 was digested with BamHI and overhanging ends were filled in with Klenow. From plasmid pKK3 (Example 1.) the sacB gene was isolated by digestion with NcoI and PstI. These sites were blunted with Klenow. A blunt end ligation was performed resulting in plasmid pKR. The plasmid pKR encodes the in frame construct of the pr-s levansucrase fusion. The fusion is in the correct reading frame which was confirmed by sequence analyses. The construct codes for the following amino acids sequence: MNFLKSFPFYAFLCFGQYFVAVTHARAS followed by the levansucrase protein sequence starting with methionine, alanine and the rest of the mature levansucrase protein (Steinmetz M. et al., supra). This construct was digested with XbaI and then partially digested with XhoI. The fragment containing the complete construct (35S/pr-s-sacB/NOS) was cloned into the XbaI and XhoI sites of pMOG23 (Symons et al. supra), a binary plant vector pBIN19 derivative (Bevan M., supra), resulting in plasmid pKT. Transgenic plants, named KT plants, which contain the construct described were generated as described in Example 1.

3. Analysis of KT plants.

Screening of the transformants, using the TLC method as in Example 1, showed accumulation of fructan with the normal variation due to position effect. The fructans accumulating in these plants were further studied by isolation of larger quantities (Livingstone III D. A., supra). Superose chromatography data and full acid hydrolysis followed by HPLC analysis as in Example 1 shows this fructan to be of high molecular weight and to be composed of fructose.

As in Example 1, senescing plants still contain fructans. Similarly seeds are fertile and the fructan producing property is inherited by the following generation.

EXAMPLE 4

Expression of ftf Gene in Apoplast

1. Selection of the genes.

To create plants which produce fructans, genes encoding proteins capable of producing fructans were selected. Another gene, fructosyltransferase encoded by the ftf gene (Shiroza T. and Kuramitsu H. K. et al., supra) and introduced in Example 2, was used. Since sucrose in tobacco plants is transported through the apoplast to the phloem, the intercellular space (apoplast) is a preferred site for fructan accumulation. A gene encoding a protein capable of targeting itself to the apoplast was selected: the pathogenesis-related protein S, encoded by the pr-s gene (Cornelissen B. J. C. et al. supra). From this gene the signal sequence was used.

2. Construction of 35S/pr-s-ftf/NOS in binary vector (pTT)

Plasmid pPB1 (Example 3.) was digested with BamHI and overhanging ends were filled in with Klenow. From plasmid pTK1 (Example 2.) the ftf gene was isolated by digestion with NcoI and PstI. These sites were blunted with Klenow. A blunt end ligation was performed resulting in plasmid pTR. The plasmid pTR encodes the in frame construct of the pr-s fructosyltransferase fusion. The fusion is in the correct reading frame which was confirmed by sequence analyses. The construct encodes for the following amino acids sequence: MNFLKSFPFYAFLCFGQYFVAVTHARAS and fructosyltransferase protein sequence starting with the methionine of the mature fructosyltransferase (Shiroza T., supra)

This construct was digested with XbaI and HindIII. The fragment containing the complete construct (35S/pr-s-ftf/NOS) was cloned into the XbaI and HindIII site of pMOG23 (Symons et al., supra), a binary plant vector pBIN19 derivative (Bevan M., supra), resulting in plasmid pTT. Transgenic plants, named TT plants, which contain the construct described were generated as described in Example 1.

3. Analysis of TT plants.

Screening of the transformants, using the TLC method as in Example 1 showed accumulation of fructan with the normal variation due to position effect.

The fructans accumulating in these plants were further studied by isolation of larger quantities (Livingstone III D. A., supra). Superose chromatography data and full acid hydrolysis followed by HPLC analysis as in Example 1 shows this fructan to be of high molecular weight and to be composed of fructose.

As in Example 1, senescing plants still contain fructans. Similarly seeds are fertile and the fructan producing property is inherited by the following generation.

EXAMPLE 5

Expression of sacB in the Cytoplasma

1. Selection of the genes.

To create plants which produce fructans, genes encoding proteins capable of producing fructans were selected. One of these genes, levansucrase encoded by the sacB gene (Steinmetz M. et al., supra) and described in Example 1, was used.

Since sucrose in plant cells is synthesized in the cytoplasm, the cytoplasm is a preferred site for fructan accumulation. Since nuclear-encoded proteins are made in the cytoplasm no targeting sequence is needed.

2. Construction of 35S-sacB-NOS in binary vector (pKZ)

Plasmid pPA2 (Example 1) was digested with NcoI and BamHI and the vector-containing fragment was isolated. From plasmid pKK3 (Example 1) the sacB gene was isolated as a NcoI and BamHI fragment. Both fragments were ligated resulting in plasmid pKX. The resulting plasmid pKX encodes the construct of mature levansucrase. The construct is correct which was confirmed by sequence analyses.

This construct was digested with XbaI and XhoI. The fragment containing the complete construct (35S-sacB-NOS) was cloned into the XbaI and XhoI site of pMOG23 (Symons et al., supra), a binary plant vector pBIN19 derivative (Bevan M., supra) resulting in plasmid pKZ.

Transgenic plants, named KT plants, which contain the construct described were generated as described in Example 1.

3. Analysis of KT plants.

Screening of the transformants, using the TLC method as in Example 1, showed accumulation of fructan with the normal variation due to position effect.

The fructans accumulating in these plants were further studied by isolation of larger quantities (Livingstone III D. A., supra). Superose chromatography data and full acid hydrolysis followed by HPLC analysis as in Example 1 shows this fructan to be of high molecular weight and to be composed of fructose.

As in Example 1, senescing plants still contain fructans. Similarly seeds are fertile and the fructan producing property is inherited by the following generation.

EXAMPLE 6

Expression of ftf gene in Cytoplasm

1. Selection of the genes.

To create plants which produce fructans, genes encoding proteins capable of producing fructans were selected. Another gene, fructosyltransferase encoded by the ftf gene (Shiroza T. and Kuramitsu H. K., supra) and introduced in Example 2, was used. Since sucrose in plant cells is synthesized in the cytoplasm, the cytoplasm is a preferred site for fructan accumulation. Since nuclear-encoded proteins are made in the cytoplasm no targeting sequence is needed.

2. Construction of 35S-ftf-NOS in binary vector (pTZ)

Plasmid pPA2 (Example 1) was digested with NcoI and BamHI and the vector-containing fragment was isolated. From plasmid pTK1 (Example 2) the ftf gene was isolated as a NcoI and BamHI fragment. Then both fragments were ligated resulting in plasmid pTX. The resulting plasmid pTX encodes the construct of mature fructosyltransferase. The construct is correct which was confirmed by sequence analyses.

This construct was digested with XbaI and HindIII. The fragment containing the complete construct (35S-ftf-NOS) was cloned into the XbaI and HindIII site of pMOG23 (Symons et al., supra), a binary plant vector pBIN19 derivative (Bevan M., supra), resulting in plasmid pTZ.

Transgenic plants, named TZ plants, which contain the construct described were generated as described in Example 1.

3. Analysis of TZ plants.

Screening of the transformants, using the TLC method as in Example 1, showed accumulation of fructan with the normal variation due to position effect.

The fructans accumulating in these plants were further studied by isolation of larger quantities (Livingstone III D. A., supra). Superose chromatography data and full acid hydrolysis followed by HPLC analysis as in Example 1 shows this fructan to be of high molecular weight and to be composed of fructose.

As in Example 1, senescing plants still contain fructans. Similarly seeds are fertile and the fructan producing property is inherited by the following generation.

EXAMPLE 7

Acquired Properties of Transgenic Tobacco Plants Harbouring Fructosyltransferase Constructs 1. General properties The transgenic tobacco plant lines harbouring the different fructosyltransferase constructs as described in examples 1–6 all accumulate fructan molecules. The level of fructan accumulation differed between individual transformants probably due to the effect of the integration site of the transgene on gene expression (position effect) and between the six different constructs used. Using Southern hybridization analysis (Sambrook, et al., supra) the number of DNA copies integrated into the individual plant genomes was determined. The number of copies integrations varied between 1–8, but most plants contained only one or two copies of the construct. The degree of polymerisation of the fructans is up to 25.000 or more fructose units. Fructans are accumulated in all organs tested, including leaves, stem, roots and in the seeds. The property was transmitted to the offspring in an Mendelian manner.

The identity of the fructans was confirmed by sizing, hydrolysis and by proton nuclear magnetic resonance spectroscopy as described in the above examples. In addition antibodies directed against fructofuranosyl linkages (Hall, B. et al. 1990, Mol.Immunology 27: 351–361; Hall, B. et al. 1992, The Journal of Immunology 149: 1605–1612) reacted with the fructans produced in the transgenic plants. For this investigation fructans were spotted on nitrocellulose filter paper and immobilized by a 15 minutes treatment at 120° C. The filters were incubated with the specific mouse antibody (Hall et al., supra) and the binding of antibodies to the fructan detected with an alkaline phosphatase conjugated goat second antibody directed against the non-specific parts of the mouse antibody.

Fructans are present throughout the life cycle of the plant. Once synthesized the fructan is stable. If there is fructan turnover at all this level will be very low. In senescent dehydrated leaves fructans are still present in amounts comparable to levels in mature leaves. The fructan content in the transgenic tobacco plants is in the range of 3–8% of the dry weigth in mature leaves. The levels of the other soluble carbohydrates (glucose, sucrose and fructose) were quantitated using HPLC chromatogray as described and were found to be comparable to the untransfomed wildtype plants.

2. Phenotypic characterisation

Under normal growth conditions no difference in growth or morphology was observed between the untransformed control tobacco plants and the fructan accumulating transgenic plants which harbour the S. mutans ftf gene in the three different configurations mentioned in Examples 2, 4 and 6 (TP, TZ and TT lines). This is also true for plants harbouring the B. subtilis sacB gene fused to the cpy targeting signal (KP plants, Example 1). Plant expressing the B. subtilis sacB gene in the cytoplasm or apoplast (KZ, KT, Examples 3 and 5) show necrotic lesions in mature leaves and stems. The severity of the phenotype correlates with the level of fructans accumulated. These plants do produce fertile seeds.

EXAMPLE 8

Enhanced Performance Under Stress Conditions of Transgenic Tobacco Plants Harbouring Fructosyltransferase Constructs The performance under stress conditions of representative fructan accumulating tobacco lines harbouring the cpy-sacB construct (KP, Example 1) was compared with un-transformed control plants.

1. Drought stress

Drought stress was induced in series of plants by the controlled addition to plants grown on vermiculite of Poly Ethylene Glycol with a mean Molecular Weight of 10.000 dalton (PEG10.000). A range of drought stress levels was induced up to 20% PEG10.000 by application of PEG solutions. Fresh weight and dry weight was determined as well as growth rate (in cm/day). The drought stressed fructan accumulating KP plants grew faster and gave significantly higher yields than similarly stressed non-transformed plants. When compared to similarly stressed non-transformed plants the transgenic KP plant fresh weigth increased in a typical case up to 19% and dry weight up to 32%.

2. Light stress conditions

Yield characteristics under suboptimal light conditions were compared between representative transgenic KP plants and non-transformed plants. The KP plants grown under low light (5000 lux) were directly compared to control (non-transformed) plants. The fructan accumulating KP plants grew faster and gave significantly higher yields than non-transformed plants. Both fresh weight and the dry weight of the KP plants was 18% higher than in non-transformed plants. The KP produced more leaves than the non-transformed plants.

High light intensities, especially when combined with suboptimal growth conditions also results in severe stress in most plant species. Fructan accumulating plants may under such conditions perform better than non-transformed plants. For example fructans function as an additional carbohydrate sink and in this way may protect against light induced damage to plants.

3. Cold stress

Growth characteristics of transgenic KP plants and non-transformed plants were compared under cold stress conditions. When grown under controlled condition at 12° C. the KP plants gave over 19% higher yields in terms of fresh weight and dry weight than non-transformed plants.

The stress conditions named under 1), 2) and 3) induced a more than four-fold increase in the level of fructan in the the transgenic KP plants compared to unstressed KP plants. The accumulation of fructans results in improved growth performance, the degree of fructan accumulation being correlated with the degree of growth enhancement.

Better performance under stress conditions may not be limited to the specific examples given under 1), 2) and 3) but may occur under a wide range of unfavourable environmental conditions. Improved performance is not limited to increased growth rates or increases in fresh and dry weight but may include other economically important physiological aspects both with respect to pre- and post-harvest properties.

In addition to improved performance under abiotic stresses as the ones mentioned above, the fructan accumulating plants may also provide the plants with enhanced resistance against biotic stresses, like diseases and pests (Farrar, in: Pests and pathogens: plant response to foliar attack, p. 107–127. Ed. P. G. Ayres, BIOS Publishers 1992). Fructan accumulation may result in metabolic or structural modifications in plants resulting in reduced sensitivity to diseases and pests. Examples of such modifications include but are not limited to changes in digestibility, texture, flavour and altered levels of other plant primary and secondary metabolic products.

Plants with natural or induced modified carbohydrate partitioning patterns may be preferred targets for improved performance under stress conditions due, for example, to further increases in fructan accumulation. Such plants include but are not limited to natural mutants in starch and sucrose metabolism and plants in which starch and sucrose metabolism have been modified by molecular and genetic techniques for example as described in Sonnewald and Will-mitzer, Plant Physiology 99, 1267–1270, 1992.

EXAMPLE 9

General Applicability of the Technology

1. The construct

To demonstrate the general applicability of the technology use was made of the cpy-sacB construct as described in Example 1. Other genes of any origin that encode polypeptides able to synthesize fructan, minimally consisting of two linked fructose units, can be used as well. In addition, the effectiveness of the introduced constructs in terms of its ability to direct fructan accumulation in transgenic plants with respect to level, timing and location can be modified by using regulatory signals which include but are not limited to constitutive promoters, organ specific promoters, developmentally regulated promoters, polyadenylation signals, translational enhancers, transcriptional enhancers etc. In addition the cellular localization of the polypeptide can be directed by using different cellular targeting signals which include but are not limited to vacuolar and apoplastic targeting signals of any origin. After introduction into plants of any combination of the above mentioned elements significant quantities of fructans can accumulate in vegetative organs which include leaves, roots and stems as well as derived organs which include but are not limited to tubers, storage roots, the fruits as well as seeds.

2. Application in different crop species

To demonstrate the general applicability of the technology the construct cpy-sacB as described in Example 1 was introduced into crop species like potato (*Solanum tuberosum* L.) of which the transformation can be but does not need to be carried out as described in Visser, Plant Tissue Culture Manual B5, 1–9, Kluwer Academic Publishers, 1991. The resulting transgenic plants accumulated fructans in every organ throughout development. Levels in leaves and tuber can be over 9% of the fresh weight. In addition the same construct was introduced into beet (*Beta vulgaris* L.) which can be but does not need to be transformed as described by D'Halluin et al. Biotechnology 10, 309–314 (1992). The resulting transgenic beet plants accumulated significant levels of fructan with a degree of polymerization up to 25.000 or more in for example their leaves and storage roots. The same cpy-sacB construct was introduced into fodder brassica (*Brassica napus* L.) which can be but does not need to be transformed as described by de Block et al. Plant Physiol 91, 694–701 (1989). The resulting transgenic fodder brassica plants accumulated significant levels of fructans with a degree of polymerization up to 25.000 or more in for example their leaves and storage organs.

In addition plant species that can be modified to accumulate fructans include but are not limited to maize (*Zea may* L.), wheat (*Triticum aestivum* L.), barley (*Hordeum vulgare* L.), rice (*Oryza sativa* L.) soybean (*Glycin max* L.), pea (*Pisum sativum* L.), bean (*Phaseolus vulgaris* L.) chicory (*Cichorium intybus* L.), sugarcane (*Saccharum officinarum* L.), yam (*Dioscorea esculenta* L.), cassave (*Manihot esculenta* L.) and grasses (e.g. *Lolium spp., Poa spp.* and *Festuca spp.*).

Plants with natural or induced modified carbohydrate partitioning patterns may be preferred targets for modification of fructan metabolism, especially increased levels of fructan accumulation. Such plants include but are not limited to natural mutants in starch and sucrose metabolism and plants in which starch and sucrose metabolism have been modified by molecular and genetic techniques for example as described in Sonnewald and Willmitzer, Plant Physiology 99, 1267–1270, 1992.

We claim:

1. A method for obtaining transgenic plants showing a distribution cf fructan in their plant tissues and plant cell compartments differing from the distribution found in non-transformed plants, comprising the steps of:

a) preparing a DNA construct comprising one or more fructosyltransferase genes, wherein the 5' untranslated region of the fructosyltransferase gene is deleted from the gene, operably linked to a promoter sequence active in plants and a terminator sequence active in plants;

b) transforming a plant cell with the construct; and c) regenerating a transgenic plant from the transforned plant cell.

2. The method as claimed in claim 1, characterized in that the DNA construct also comprises a targeting sequence upstream from the fructosyltransferase gene.

3. The method as claimed in claim 1, characterized in that the fructosyltransferase gene originates from a micro-organism.

4. The method as claimed in claim 3, characterized in that the fructosyltransferase gene is selected from the group consisting of the sacB gene of *Bacillus subtilis* and the ftf gene of *Streptococcus mutants*.

5. The method as claimed in claim 1, characterized in that the fructosyltransferase gene originates from a plant.

6. The method as claimed in claim 2, characterized in that the targeting sequence is selected from the group consisting of the signal sequence and vacuolar targeting sequence of the carboxypeptidase Y gene, and the signal sequence and apoplasmatic targeting sequence of the pathogenesis-related protein S gene.

7. The method as claimed in claim 1, characterized in that the terminator sequence is a nopaline synthase gene terminator sequence.

8. The method as claimed in claim 1, characterized in that the promoter sequence is a constitutive or regulable promoter sequence.

9. The method as claimed in claim 1, characterized in that the promoter sequence is selected from the group consisting of the 35S Cauliflower Mosaic Virus promoter sequence and the potato granule-bound starch synthase promoter.

10. The method as claimed in claim 1, characterized in that the DNA construct also comprises a translational enhancer sequence upstream from the fructosyltransferase gene and downstream from the promoter sequence.

11. The method as claimed in claim 10, characterized in that the translational enhancer sequence is a Alfalfa Mosaic Virus RNA4 translational enhancer.

12. A DNA construct for the production of transgenic plants, comprising one or more fructosyltransferase genes, wherein the 5' untranslated region of the fructosyltransferase gene is deleted from the gene, operably linked to a plant specific promoter sequence and a plant specific terminator sequence.

13. The DNA construct as claimed in claim 12, also comprising a targeting sequence upstream from the fructosyltransferase gene.

14. A transgenic plant cell comprising a DNA construct as claimed in claim 12.

15. A transgenic plant produced according to the method of claim 1.

16. Transgenic plant tissue of a plant as claimed in claim 15.

17. Transgenic plant tissue as claimed in claim 16, selected from the group consisting of fruit, stem, root, tuber, seed and leaf.

18. A plant cultured under conditions of abiotic stress comprising a transgenic plant prepared in accordance with the method of claim 1, wherein the transgenic plant has a distribution of fructan in its plant tissues and plant cell compartments differing from the distribution of fructan found in non-transformed plants.

19. A source for the production and extraction of fructans comprising a transgenic plant prepared in accordance with the method of claim 1, wherein the transgenic plant has a distribution of fructan in its plant tissues and plant cell compartments differing from the distribution of fructan found in non-transformed plants.

20. Transgenic seed comprising seed produced by a transgenic plant prepared in accordance with the method of claim 1, wherein the transgenic plant has a distribution of fructan in its plant tissues and plant cell compartments differing from the distribution of fructan found in non-transformed plants.

21. A transgenic plant produced in accordance with the method of claim 1, wherein the transgenic plant has an increased tolerance for temperature variations.

22. A transgenic plant produced in accordance with the method of claim 1, wherein the transgenic plant has an increased tolerance for abiotic stress.

23. A method for obtaining a transgenic plant showing a distribution of fructan in its plant tissues and plant cell compartments differing from the distribution found in non-transforrned plants, comprising the steps of:

(a) preparing a DNA construct comprising the sacB fructosyltransferase gene of *Bacillus subtilis*, modified such that the 5' untranslated region of the sacB gene is deleted, operably linked to a promoter sequence active in plants and a terminator sequence active in plants;

(b) transforming a plant cell with the construct; and (c) regenerating a transgenic plant from the transforned plant cell.

24. The method of claim 23, characterized in that the DNA construct also comprises a targeting sequence upstream from the fructosyltransferase gene.

25. The method of claim 24, characterized in that the targeting sequence is selected from the group consisting of the signal sequence and vacuolar targeting sequence of the carboxypeptidase Y gene and the signal sequence and apoplasmatic targeting sequence of the pathogenesis-related protein S gene.

26. The method of claim 23, characterized in that the promoter sequence is selected from the group consisting of 35S Cauliflower Mosaic Virus promoter sequence and the Potato Granule-Bound Starch-Synthase promoter.

27. The method of claim 23, characterized in that the DNA construct also comprises a translational enhancer sequence upstream from the fructosyltransferase gene and downstream from the promoter sequence.

28. The method of claim 27, characterized in that the translational enhancer sequence is an Alfalfa Mosaic Virus RNA4 translational enhancer.

29. A DNA construct for the production of transgenic plants, comprising the sacB fructosyltransferase gene of *Bacillus subtilis*, modified such that the 5' untranslated region of the gene is deleted, operably linked to a plant-specific promoter sequence and a plant specicic terminator sequence.

* * * * *

UNITED STATES PATENT AND TRADEMARK OFFICE
CERTIFICATE OF CORRECTION

PATENT NO. : 6,025,542  
DATED : February 15, 2000  
INVENTOR(S) : J.C.M. Smeekens et al.

Page 1 of 4

It is certified that error appears in the above-indentified patent and that said Letters Patent is hereby corrected as shown below:

| COLUMN | LINE | |
|---|---|---|
| [56]<br>Pg. 1, col. 2 | Refs. Cited<br>(Other Refs.,<br>Item 3) | "Glucoysltransferases:" should read<br>--Glucosyltransferases:-- |
| [56]<br>Pg. 1, col. 2 | Refs. Cited<br>(Other Refs.,<br>Item 4) | "et al," should read --et al.,-- |
| [56]<br>Pg. 2, col. 1 | Refs. Cited<br>(Other Refs.,<br>Item 10) | "physioloical" should read --physiological-- |
| [56]<br>Pg. 2, col. 1 | Refs. Cited<br>(Other Refs.,<br>Item 10) | "*Sci.Nutr.*" should read --*Sci. Nutr.*-- |
| [56]<br>Pg. 2, col. 1 | Refs. Cited<br>(Other Refs.,<br>Item 11) | "fructo-oligosaccharaides" should read<br>--fructo-oligosaccharides-- |
| [56]<br>Pg. 2, col. 1 | Refs. Cited<br>(Other Refs.,<br>Item 11) | "120(5) :" should read --120(5):-- |
| [56]<br>Pg. 2, col. 1 | Refs. Cited<br>(Other Refs.,<br>Item 11) | "Jan.31,1994." should read --Jan. 31, 1994.-- |

UNITED STATES PATENT AND TRADEMARK OFFICE
CERTIFICATE OF CORRECTION

PATENT NO. : 6,025,542  Page 2 of 4
DATED : February 15, 2000
INVENTOR(S) : J.C.M. Smeekens et al.

It is certified that error appears in the above-indentified patent and that said Letters Patent is hereby corrected as shown below:

| COLUMN | LINE | |
|---|---|---|
| [56] Pg. 2, col. 1 | Refs. Cited (Other Refs., Item 12) | delete ""Bifidus growth-stimulating substances," *Chemical Abstracts*, 100(17):137377, Apr. 23, 1994." |
| [56] Pg. 2, col. 1 | Refs. Cited (Other Refs., Item 14) | "Trangenic" should read --Transgenic-- |
| [56] Pg. 2, col. 2 | Refs. Cited (Other Refs., Item 15) | "NRRL-1678" should read --NRRL B-1678-- |
| [56] Pg. 2, col. 2 | Refs. Cited (Other Refs., Items 18-20) | "Steinmetz et al 1985 Mol Gen Genet 200:220-228. Shiroza et al 1988 J of Bacti 170(2):810-816. Fuchs 1991 Biochem Soc. Transactions 19:555-560. Smeekens et al 1991 Biochem Soc Transactions 19:565-569.-" should read --Steinmetz et al., 1985 *Mol. Gen. Genet.* 200:220-228. Shiroza et al., 1988 *J. of Bacti.* 170(2):810-816. Fuchs, 1991 *Biochem. Soc. Transactions* 19:555-560. Smeekens et al., 1991 *Biochem. Soc. Transactions* 19:565-569.-- |

UNITED STATES PATENT AND TRADEMARK OFFICE
CERTIFICATE OF CORRECTION

PATENT NO. : 6,025,542
DATED : February 15, 2000
INVENTOR(S) : J.C.M. Smeekens et al.

It is certified that error appears in the above-indentified patent and that said Letters Patent is hereby corrected as shown below:

| COLUMN | LINE | |
|---|---|---|
| 16 (Claim 1, | 49 line 2) | "cf" should read --of-- |
| 16 (Claim 1, | 58 line 11) | "transforned" should read --transformed-- |
| 17 (Claim 4, | 2 line 4) | "*mutants*" should read --*mutans*-- |
| 17 (Claim 10, | 24 line 4) | "downstrearn" should read --downstream-- |
| 17 (Claim 11 | 26 line 2) | "a Alfalfa" should read --an Alfalfa-- |
| 18 (Claim 23 | 18 line 4) | "transforrned" should read --transformed-- |
| 18 (Claim 23 | 26 line 11) | "transforned" should read --transformed-- |
| 18 (Claim 25 | 34 line 4) | after "Y gene" insert --,-- |

UNITED STATES PATENT AND TRADEMARK OFFICE
CERTIFICATE OF CORRECTION

PATENT NO. : 6,025,542
DATED : February 15, 2000
INVENTOR(S) : J.C.M. Smeekens et al.

It is certified that error appears in the above-indentified patent and that said Letters Patent is hereby corrected as shown below:

COLUMN    LINE

18            52          "specicic" should read --specific--
(Claim 29  line 5)

Signed and Sealed this

Third Day of April, 2001

Attest:

NICHOLAS P. GODICI

Attesting Officer      Acting Director of the United States Patent and Trademark Office